United States Patent

Cabri et al.

[11] Patent Number: 5,916,897
[45] Date of Patent: Jun. 29, 1999

[54] PROCESS FOR THE PREPARATION OF 9-AMINO CAMPTOTHECIN

[75] Inventors: Walter Cabri, Rozzano; Ilaria Candiani, Busto Arsizio; Franco Zarini, Settimo Milanese; Angelo Bedeschi; Sergio Penco, both of Milan, all of Italy

[73] Assignee: Pharmacia & Upjohn S.p.A., Milan, Italy

[21] Appl. No.: 08/775,605

[22] Filed: Dec. 31, 1996

Related U.S. Application Data

[62] Division of application No. 08/313,960, Sep. 28, 1994, Pat. No. 5,614,628.

[30] Foreign Application Priority Data

Sep. 28, 1993 [GB] United Kingdom ............... 9311944

[51] Int. Cl.⁶ .............................................. C07D 491/147
[52] U.S. Cl. .............................................. 514/283; 546/48
[58] Field of Search .................................. 546/48; 514/283

[56] References Cited

U.S. PATENT DOCUMENTS

| | | | |
|---|---|---|---|
| 5,602,141 | 2/1997 | Bedeschi et al. | 514/283 |
| 5,614,628 | 3/1997 | Cabri et al. | 546/48 |

*Primary Examiner*—Donald G. Daus
*Attorney, Agent, or Firm*—Oblon, Spivak, McClelland, Maier & Neustadt, P.C.

[57] ABSTRACT

The present invention relates to compounds of the following formulas:

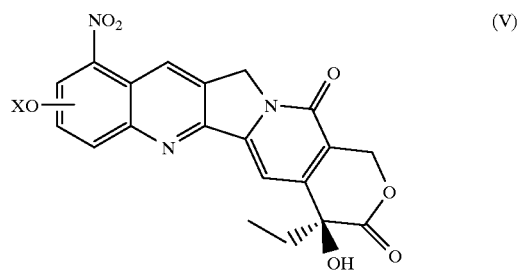

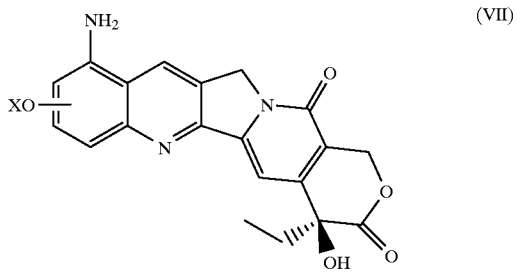

which are endowed with antitumor activity. The invention also relates to methods of treating tumors using these compounds.

6 Claims, No Drawings

PROCESS FOR THE PREPARATION OF 9-AMINO CAMPTOTHECIN

This is a Division, of application Ser. No. 08/313,960 filed on Sep. 28, 1994, now U.S. Pat. No. 5,614,628.

FIELD OF THE INVENTION

The present invention relates to a new process for the preparation of 9-amino-20(S)-camptothecin of formula (I)

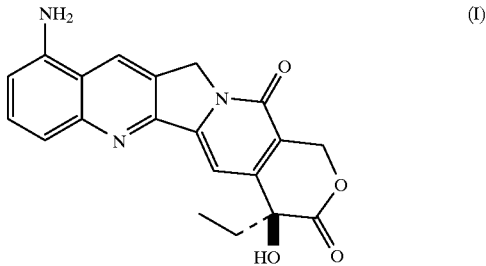

which is a known antitumor agent: Wani et al, J. Med. Chem. 1987, 30, 1774–1779; Hsiang et al., Cancer Res. 49, 4385–4389, Aug. 15, 1989; Cancer Res. 49, 1465–1469, Mar. 15, 1989.

BACKGROUND OF THE INVENTION

Totally synthetic approaches to 9-amino camptothecin have been widely described (U.S. Pat. No. 4,894,456 and U.S. Pat. No. 5,053,512). Total synthesis of the product, however, is neither desirable nor suitable for large scale production because it involves too many process steps that make the synthesis too long and, especially, too expensive.

A semisynthetic approach to 9-amino camptothecin is described, e.g. in JP-A-59-51288 and JP-A-59-51289, both published in 1984, starting from the known natural product camptothecin: Cancer Chemotherapy Reports, part I, vol. 54, No. 6, December 1970, 461–470; J. Med. Chem., 1980, 23, 554–560; Science, vol. 246, November 1989, 1046–1048. The natural 20(S)-camptothecin has the following formula (II)

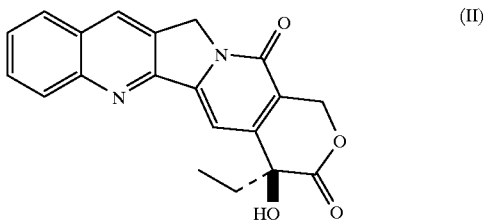

The said semisynthetic approach involves the nitration of the naturally occurring camptothecin, followed by reduction of the 9-nitro derivative. That nitration, however, initially produces a 70/30 mixture of the undesired 12-nitro camptothecin derivative (70%) and of the desired 9-nitro camptothecin derivative (30%). The 9-nitro derivative is therefore formed only in a minor amount.

After the separation of the two nitration products, the 12-nitro derivative, which is itself biologically inactive (see, for instance, Wani C., Nicholas A. W., Wall M. E., J. Med. Chem., 1986, 29, 2358), must then be discharged, giving rise to waste treatment problems. The considerable drawback concerning the removal of the undesired 12-nitro derivative byproduct is particularly relevant for large scale production since large amounts of unuseful 12-nitro derivative are collected and need to be eliminated.

Moreover, following this semisynthetic approach, large quantities of natural camptothecin which is highly expensive, are needed to produce small quantities of the desired antitumor agent 9-amino camptothecin. The low overall productivity and yields of this approach make the production of substantial amounts of the desired compound difficult. There is therefore a need for a process permitting increased productivity and yields compared to the above outlined semisynthetic approach to 9-amino camptothecin.

SUMMARY OF THE INVENTION

According to the present invention, there is provided a new process for preparing 9-amino camptothecin of formula (I) starting from 10- or 12-hydroxy-20(S)-camptothecin of formula (III), according to the steps illustrated in Scheme I below:

Scheme I

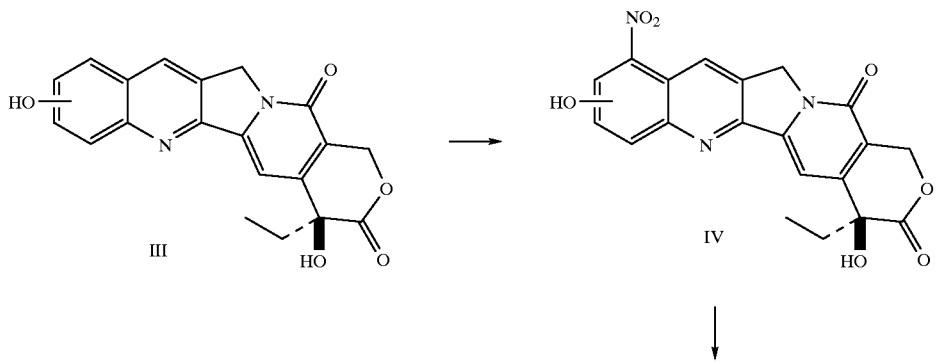

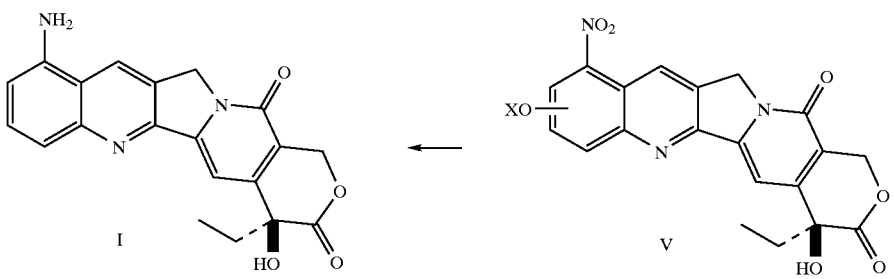

wherein XO is a group which can be removed reductively. Removal reductively means that the XO group may be removed by reduction with a homogenous or heterogenous catalyst. After removal reductively, the replaced XO group is thus by a hydrogen atom.

This process allows the synthesis of 9-amino-20(S)-camptothecin in high yield and productivity. The process is characterized by easy and mild reaction conditions ensuring high yields and clean reaction products. Especially in the last step, the benzylic oxygens and the lactone moiety (which are essential for the biological activity) survive the reductive removal of the OX group intact. Moreover the nitration reaction, due to the presence of the hydroxy moiety, proceeds with high regioselectivity and under easy and mild conditions which are also much safer than the usual nitration reaction conditions. The correct 20(S)-configuration is conserved throughout the process.

DETAILED DESCRIPTION OF THE INVENTION

The present invention provides a process for preparing the 9-amino camptothecin of formula (I)

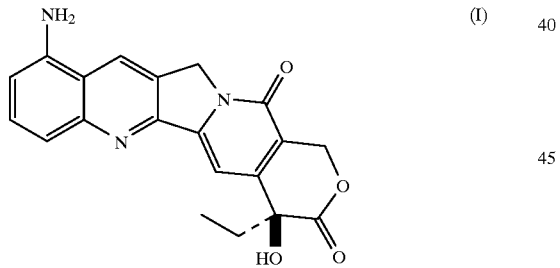

said process comprising:

(1) reacting a compound of formula (III)

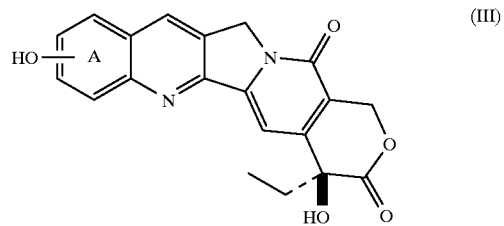

wherein the hydroxy group on ring A is in the 10- or 12-position, with a nitrating agent, so obtaining a corresponding compound of formula (IV)

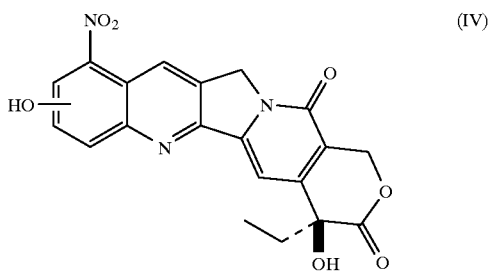

(2) converting the compound of formula (IV) into a corresponding compound of formula (V)

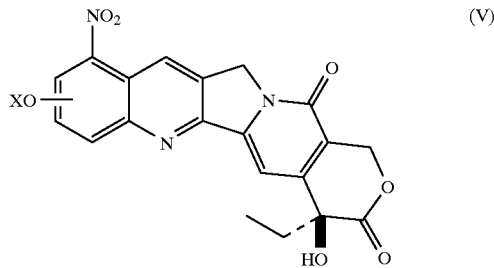

wherein XO is a group that can be removed reductively; and (3) reductively removing the said XO group and reducing the nitro group of the compound of formula (V), so obtaining the 9-amino camptothecin of formula (I).

This process has never been exploited before, and especially the double reductive step with simultaneous deoxygenation and nitro group reduction is not known. In J. Med Chem. 34, 98, 1991, deoxygenation of a 10-triflate-9-N,N-dimethylaminomethyl derivative of camptothecin in the presence of tetrakistriphenylphosphine Pd(O) is described. However the reaction had very low yields (20%). Moreover the preparation of this triflate may be a major problem in term of selectivity and stability, limiting drastically its usefulness (see for instance Subramanian, L. R., et al, Synthesis 293, 1973).

While the reductive deoxygenation in the presence of tetrakistriphenylphosphine Pd(O) is well known in organic chemistry (see for instance Cacchi, S. et al., Tetrahedron Letters 27, 5541, 1986), we have shown that other more suitable sulfonates are unreactive under these conditions (see for instance Cabri, W. et al., J. Org. Chem. 55, 350, 1990). The use of different phosphines or sulfonates has been never reported on a camptothecin and their usefulness was unpredictable on the basis of the current literature. Moreover it is known that the presence of a nitro group in o- or p-position to the sulfonate ester may cause lower yields than usual in Heck type reactions (see for instance J. Org. Chem. 57, 1481, 1992 and Echavarren, A. M.; Stille, J. K.; J. Am. Chem. Soc 109, 5478, 1987).

Surprisingly, the deoxygenative reduction in the present process can take place using the less reactive sulphonates, not described before, under milder conditions and affording in good yield the desired product in spite of the presence of the nitro group. Surprisingly the nitro group itself can undergo reduction in the reaction medium. In one single step the desired 9-amino derivative can be obtained without the necessity of further reactions. This concomitant reduction of the nitro group was previously unknown and, in the light of the current literature, unpredictable (see for instance Cacchi, S., et al., Tetrahedron Letters 27, 5541, 1986).

The starting compound of the present process is the compound of formula (III). This has a 20(S)-configuration which is retained throughout the process. The compound of formula (III) is typically free of the corresponding 20(R)-isomer. However, the present invention may be applied to a racemic mixture of the compound of formula (III) and the corresponding 20(R)-isomer. In that case, a racemic mixture of 9-amino-20(S)-camptothecin of formula (I) and 9-amino-20(R)-camptothecin is obtained. The compound of formula (III) may be obtained by known methodologies from 20(S)-camptothecin (see for instance JP-A-59-51288; JP-A-59-51299; J. Med. Chem. 34, 98, 1991; and Chem. Pharm. Bull. 1991, 39, 3183, 1991).

Further, 12-hydroxy-20(S)-camptothecin can be prepared from the known 12-nitro-20(S)-camptothecin. The 12-nitro-20(S)-camptothecin is first reduced to 12-amino-20 (S)-camptothecin. The reduction may be carried out, for example, with suitable reducing agents, or by catalytic reduction with suitable catalysts, in the presence of suitable reducing agents. For example, it may be performed as described in: J. March, Advanced Organic Chemistry, Third Edition, 1103.

For instance, the reduction may be performed with reducing agents such as $SnCl_2$, or other metals or metal salts, such as Zn or Fe and their salts, in a suitable solvent such as dilute aqueous HCl, dilute aqueous protic acids, water, ethanol, methanol, or mixtures thereof, at a temperature of from $-20°$ C. to $60°$ C., for a period of from few minutes to several days such as from 5 mins to 3 days, for example from 4 hours to 24 hours.

Alternatively the reduction may be performed by the use of catalytic amounts of metals which perform nitro group reduction, such as, palladium, platinum oxide, platinum, rhodium or ruthenium, in the presence of molecular hydrogen or hydrogen sources, such as triethylammonium formate, formic acid, tributyltin hydride, cyclohexadiene, etc., in a suitable solvent, such as dimethylformamide (DMF), MeOH, acetic acid, $CHCl_3$, dioxane, or mixtures thereof, at a temperature of from about $0°$ C. to $100°$ C., for a time of from 1 hour to 3 days, and at a pressure of from 1 atm to 100 atm.

The 12-amino-20(S)-camptothecin may be converted into 12-hydroxy-20(S)-camptothecin with a suitable reagent such as, for example, a copper(I) oxide, through the formation of a diazoderivative which does not need to be isolated from the reaction mixture.

The diazotisation reaction may be performed by the use of suitable diazotising agents, such as $NaNO_2$, organic nitrites in aqueous dilute protic acids, such as HCl or $H_2SO_4$, or in organic solvents, at a temperature of from $-20°$ C. to $100°$ C., for a period of from a few minutes to several hours such as from 5 mins to 24 hours. The resulting solution may then be reacted with from a stoichiometric amount to a large excess, for example up to a 10-fold molar excess, of copper (I) oxide, optionally in the presence of an aqueous solution of copper(I) nitrate, at a temperature of from $0°$ C. to $100°$ C., for from a few minutes to 1 day such as from 5 minutes to 1 day.

The compound of formula (III) can be reacted with suitable common nitrating agents to give the compound of formula (IV). The nitration of a compound of formula (III) may be performed with a nitrating agent, such as nitric acid, mixtures of nitric and sulphuric acid, or other nitrating agents, such as potassium nitrate or nitric acid and boron trifluoride such as boron trifluoride monohydrate (see for instance Olah, G. A., et al. Synthesis 1085, 1992), or nitric acid/trifluoromethansulfonic anhydride (ibid., 1087, 1992), at a temperature of from $-20°$ C. to $100°$ C., for a time of from a few minutes to several days such as from 5 mins to 3 days, for example from 4 hours to 24 hours.

The compound of formula (IV) is in turn converted into a corresponding compound of formula (V). This may be achieved by reacting the compound of formula (IV) with a sulfonylating agent of formula (VI)

$$X\text{—}R''\qquad\qquad(VI)$$

wherein

X is a group $R\text{—}SO_2\text{—}$ in which

R is:
(i) a phenyl or naphthyl ring which is unsubstituted or substituted by one or more substituents, for example one, two or three substituents, chosen from $C_1$–$C_5$ linear or branched alkyl, $C_1$–$C_5$ linear or branched alkoxy, halogen, hydroxy, amino and nitro; or
(ii) a linear or branched $C_1$–$C_9$ alkyl group which is unsubstituted or substituted by one or more, for example one, two or three halogen atoms; and
R" is a halogen atom, an imidazolyl group, a $\text{—}OSO_2R$ or $\text{—}N(C_6H_5)$ $(RSO_2)$ group wherein R is as defined above or another group capable of reacting with a phenol to give a sulphonate.

A $C_1$–$C_9$ alkyl group may be preferably a $C_1$–$C_5$ alkyl group such as, e.g., methyl, ethyl, n-propyl or iso-propyl. A $C_1$–$C_5$ alkoxy group may be a $C_1$–$C_4$ alkoxy group such as, e.g., methoxy, ethoxy, n-propoxy or iso-propoxy.

A halogen atom may be fluoro, chloro or bromo. A $C_1$–$C_5$ alkyl group substituted by one or more halogen atoms may be a $C_1$–$C_5$ perhaloalkyl group such as a $C_1$–$C_5$ perchloroalkyl or perfluoroalkyl group, for example, trifluoromethyl. Preferred meanings which the group X may assume when present in the compounds of the invention are chosen from optionally substituted sulfonate esters of the above formula $R\text{—}SO_2\text{—}$ wherein R is:
(i) a phenyl or naphthyl ring which is unsubstituted or substituted by one substituent chosen from $C_1$–$C_5$ linear or branched alkyl, a $C_1$–$C_5$ linear or branched alkoxy, halogen, hydroxy, amino and nitro; or
(ii) a linear $C_1$–$C_5$ alkyl group which is unsubstituted or substituted by one or more, for example one, two or three, halogen atoms which are preferably fluorine or chlorine.

More preferably the group X is $R\text{—}SO_2\text{—}$ wherein R is:
(i) a phenyl or naphthyl ring, which is unsubstituted or substituted by one substituent chosen from $C_1$–$C_5$ linear alkyl, $C_1$–$C_5$ linear alkoxy, fluorine or chlorine; or
(ii) a linear $C_1$–$C_5$ alkyl group which is unsubstituted or substituted by one or preferably more, for example two or three, fluorine atoms.

Particularly preferred meanings which the group X may assume in compounds of the present invention are chosen from the group comprising: p-methoxybenzensulfonyl, p-toluensulfonyl, p-fluorobenzensulfonyl, methansulfonyl, trifluoromethansulfonyl, benzensulfonyl, p-nitrobenzensulfonyl and 1- or 2-naphthalensulfonyl.

Preferred meanings of a compound of formula (VI) include p-methoxybenzensulfonyl chloride, p-toluensulfonyl chloride, p-fluorobenzensulfonyl chloride, methansulfonyl chloride, trifluoromethansulfonic anhydride, benzensulfonyl chloride, p-nitrobenzensulfonyl chloride, N-phenyltrifluorometane sulfonimide or 1- or 2-naphthalensulfonyl chloride.

The reaction of a compound of formula (IV) with a compound of formula (VI) to obtain a compound of formula (V) may be carried out at a temperature of from −50 to 100° C., for example from 0 to 50° C. Reaction may occur for a period of from 5 minutes to 3 days, for example from 4 hours to 24 hours. The reaction typically occurs in an anhydrous organic solvent such as $CHCl_3$, $CH_2Cl_2$, tetrahydrofuran (THF), dioxane, dimethylformamide (DMF), dimethylacetamide (DMA), etc. Optionally an organic base may be present such as pyridine, triethylamine or a sterically hindered base such as, e.g., diisopropylamine, 2,6-dimethylpyridine, etc.

Reductive removal of the XO functionality and nitro group reduction transforms the compound of formula (V) to the compound of formula (I). This may be achieved utilising suitable reducing agent(s) in the presence of suitable catalyst (s). Removal of the XO group and reduction of the nitro group to form an amino group may be carried out in a single step or in two steps. In the latter case, the removal of the XO group and the reduction of the nitro group can be carried out in any order.

The reduction may therefore be performed in two steps first by reducing the nitro functionality in a compound of formula (V), wherein X is a group R—$SO_2$— and R is as defined above, with a suitable reducing agent.

This gives a compound of formula (VII)

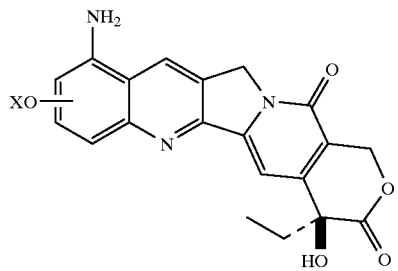

wherein X is as defined above. A deoxygenative reduction of the compound of formula (VII), for example with a suitable reducing agent, may be then performed separately affording the desired 9-amino derivative (I).

A two step reduction may also be performed, if desired, first by deoxygenating a compound of formula (V) to afford the compound of formula (VIII)

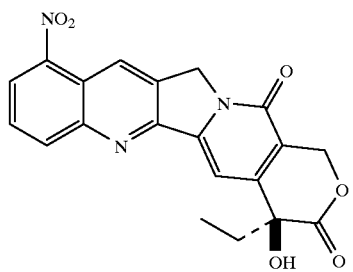

The compound of formula (VIII) may then be in turn reduced, for example with a suitable reducing agent, to the desired compound of formula (I).

Suitable reducing agents include molecular hydrogen, ammonium formate, triethylammonium formate, formic acid, tributyltin hydride, cyclohexadiene, a polymethylhydroxysilane, etc., in the presence of a suitable catalyst such as palladium, platinum oxide, platinum, rhodium or ruthenium, as such or supported on a suitable medium, such as on carbon, on $CaCO_3$, on $BaSO_4$, on alumina, etc. Alternatively, reduction may be carried out under homogeneous conditions. Reduction is then achieved by a reducing agent such as ammonium formate, triethylammonium formate, formic acid, tributyltin hydride, cyclohexadiene or a polymethylhydroxysilane in the presence of a compound of general formula (IX)

$$ML_nL'_m \qquad (IX)$$

wherein M represents a transition metal atom; L and L', which may be the same or different, may be an anion such as $Cl^-$ or $CH_3COO^-$ or a neutral molecule such as a solvent molecule, a mono or a di-phosphine, a phosphite or a diamine; and n and m may vary from 0 to 4. Typically m+n is at least 1, for example 1, 2, 3 or 4.

Preferred transition metal atoms which M may represent are palladium, nickel and platinum. Preferred groups which L and/or L' may represent are chelating diphosphines such as bis(diphenylphosphino)methane, 1,2-and 1,3-bis(diphenylphosphino)propane, 1,4-bis(diphenylphosphino)butane, 1,1'-bis(diphenylphosphino)-ferrocene or triphenylphosphine. The molar ratio of transition metal atom:chelating diphosphine is generally from 1:1 to 1:4. Suitable solvents for the reductions are organic solvents, such as DMF, MeOH, acetic acid, $CHCl_3$, dioxane, THF, or mixtures thereof, at a temperature of from about 0° C. to 200° C., for a time of from 1 hour to 3 days such as from 4 hours to 24 hours.

When the reduction is performed in two separate steps, the first step may be performed for a short time such as for times of from a few minutes to several hours for example 5 minutes to 12 hours. The intermediate derivative is isolated if desired. The second reductive step is then carried out for a time of from a few minutes to several hours, for example from 5 minutes to 12 hours. Suitable solvents for both steps are benzene, toluene, $CHCl_3$, acetonitrile, DMF, dioxane, etc. or mixtures thereof. Suitable temperatures are from room temperature to the solvent reflux temperature.

Preferred reagents for the conversion of a compound of formula (III) into a compound of formula (IV) are nitric acid, mixtures of nitric and sulphuric acid, or potassium nitrate or nitric acid and boron trifluoride monohydrate or nitric acid/trifluoromethansulfonic anhydride, at a temperature of from −20° C. to 60° C., for a time of from a few minutes to several hours such as from 5 minutes to 12 hours.

Preferred reagents for the conversion of a compound of formula (IV) to a compound of formula (V) are sulfonylating agents such as p-toluensulfonyl chloride, p-fluorobenzensulfonyl chloride, methansulfonyl chloride, trifluoromethansulfonic anhydride, benzensulfonyl chloride, p-nitrobenzensulfonyl chloride, N-phenyltrifluorometane sulfonimide or 1- or 2-naphthalensulfonyl chloride, in an anhydrous organic solvent such as $CHCl_3$, $CH_2Cl_2$, THF, dioxane, DMF, DMA, etc., at a temperature of from −20 to 80° C., for a period of from a few minutes, such as 5 minutes to 2 days. Optionally an organic base is present such as pyridine, triethylamine or a stearically hindered base such as diisopropylethylamine, or 2,6-dimethyl-pyridine.

The most preferred reagents are sulfonylating agents such as p-toluensulfonyl chloride, p-fluorobenzensulfonyl chloride or methansulfonyl chloride, in an anhydrous organic solvent such as $CHCl_3$, $CH_2Cl_2$, THF, dioxane, DMF or DMA, at a temperature of from −20 to 60° C., for a period of from few minutes, for example 5 minutes, to 1 day. The optional organic base is most preferably pyridine, triethylamine or a stearically hindered base such as diisopropylethylamine.

Preferred reducing agents for the conversion of the compound of formula (V) into the compounds of formulae (VII) and (VIII) and formula (I) are:

molecular hydrogen;

ammonium formate, triethylammonium formate, formic acid, tributyltin hydride, cyclohexadiene, a polymethylhydroxysilane, etc., in the presence of a suitable catalyst such as palladium, platinum oxide or platinum, as such or supported on a suitable medium such as on carbon, on $CaCO_3$, on $BaSO_4$, on alumina, etc.; or ammonium formate, triethylammonium formate, formic acid, a polymethylhydroxysilane or tributyltin hydride, in the presence of a catalyst of the above general formula (IX) wherein M, L, L', m and n are as defined above. The most preferred meanings for phosphorus ligands L and/or L' are 1,3-bis(diphenylphosphino) propane, 1,4-bis(diphenyl phosphino)butane, 1,1'-bis (diphenylphosphino)ferrocene or triphenylphosphine.

Suitable solvents for the reduction steps are organic solvents such as DMF, $CHCl_3$, dioxane, THF, DMSO, DMA or mixtures thereof. Preferably the temperature is from about 20° C. to 120° C. Preferably the reaction time is from 1 hour to 2 days.

The most preferred reducing agents are molecular hydrogen, triethylammonium formate, formic acid and tributyltin hydride. The most preferred solvents for the reduction steps are DMF, dioxane, THF, DMSO, DMA, or mixtures thereof.

The 9-amino camptothecin of formula (I) is a useful inhibitor of topoisomerase I. It is useful in the treatment of cancers, in particular leukemia and colon and rectal tumours. The compound may therefore be used to improve the condition of a patient suffering from such a cancer. It can be used to alleviate such a cancer.

An effective amount of the 9-amino camptothecin may thus be administered to a host in need thereof, typically a human. The active compound can be administered by any appropriate route, for example orally or parenterally such as intravenously. A dose of from 0.1 to 60 mg of active compound can be given to a human patient per kg body weight by these routes. A preferred dosage range is from 1 to 40 mg per kg body weight.

The 9-amino camptothecin of formula (I) may be formulated for administration purposes into a pharmaceutical composition with a pharmaceutically acceptable carrier or diluent. Any suitable carrier or diluent may be employed, depending upon the route of administration. Suitable types of formulations are described in U.S. Pat. No. 5,106,742 and WO 91/05556.

The present invention includes in its scope also compounds having the above reported formulae (V) and (VII) wherein X is as defined above, and the pharmaceutically acceptable salts thereof.

The compound of formulae (V) and (VII) are endowed with antitumor activity; for example, they are effective against leukemia and solid tumors such as, for example, colon and rectal tumors.

The antitumor activity of the compounds of the present invention is shown, for example, by the fact that they have been found to possess cytotoxic activity (expressed as the concentration producing 50% inhibition of cellular growth —$IC_{50}$—), when tested in vitro on L1210 murine leukemia cells after 484 continuous treatment with gradual concentrations of each molecule. The $IC_{50}$ was determined for each molecule from dose-response curves counting the total number of cells with a Coulter Counter.

For example, for the compounds of the invention 9-amino-10-(p-toluensulfonyloxy)-20(S)-camptothecin (internal code FCE 28948) and 9-nitro-10-(p-toluensulfonyloxy)-20(S)-camptothecin (internal code FCE 28899) the obtained value of $IC_{50}$ were 10.6 and 43.0 ng/ml, respectively.

A human or animal body may thus be treated by a method which comprises the administration thereto of a pharmaceutically effective amount of a compound of formula (V) or (VII) or salt thereof. The condition of the human or animal can thereby be improved.

The compounds of the invention can be administered in a variety of dosage forms, e.g. orally, in the form of tablets, capsules, lozengers, liquid solutions or suspensions; rectally, in the form of suppositories; parenterally, e.g. intramuscularly, intravenously, intradermally or subcutaneously.

The dosage depends on the age, weight and conditions of the patient and on the administration route. For example, a suitable dosage for administration to adult humans may range from about 0.1 to 60 mg per Kg of body weight, a particularly preferred range may be from about 1 to about 40 mg per Kg of body weight.

The pharmaceutical compositions of the invention contain a compound of formula (V) or (VII) as the active substance, in association with one or more pharmaceutically acceptable excipients.

The pharmaceutical compositions of the invention are usually prepared following conventional methods and are administered in a pharmaceutically suitable form. For instance, solutions for intravenous injection or infusion may contain as carrier, for example, sterile water or preferably, they may be in the form of sterile aqueous isotonic saline solutions. Suspensions or solutions for intramuscular injections may contain, together with the active compound a pharmaceutically acceptable carrier, e.g. sterile water, olive oil, ethyl oleate, glycols, e.g. propylene glycol, and if desired, a suitable amount of lidocaine hydrochloride. The solid oral forms, e.g. tablets and capsules, may contain, together with the active compound, diluents, e.g. lactose, dextrose, saccharose, cellulose, corn starch and potato starch; lubricants, e.g. silica, talc, stearic acid, magnesium or calcium stearate, and/or polyethylene glycols; binding agents, e.g. starches, arabic gums, gelatin, methylcellulose, carboxymethyl cellulose, polyvinylpyrrolidone; disaggregating agents, e.g. a starch, alginic acid, alginates, sodium starch glycolate; effervescing mixtures; dyestuffs; sweeteners; wetting agents, for instance, lecithin, polysorbates, laurylsulphates; and, in general, non-toxic and pharmacologically inactive substances used in pharmaceutical formulations. Said pharmaceutical preparations may be manufactured in a known manner, for example by means of mixing, granulating, tabletting, sugar-coating, or film-coating processes.

The following Examples illustrate the preparation of the intermediates and compounds of the present invention and do not limit the scope of the invention.

EXAMPLE 1

9-nitro-10-hydroxy-20(S)-camptothecin (Method A)

50 ml of 35% $H_2O_2$ were dropped into a suspension of 2.8 g of 20(S)-camptothecin in acetic acid. The temperature of the solution was raised to 80° C. and maintained for 3.5 hr. After cooling the solvent was evaporated until about 20 ml remain. The mixture was poured into 200 ml of water and ice. The precipitate was filtered, washed with water and ether and dried. The product was crystallized ($CHCl_3$/hexane) to give 1.9 g of 20(S)-camptothecin 1-oxide.

0.65 g of 20(S)-camptothecin 1-oxide was dissolved in 600 ml of dioxane, 8.8 ml of 1M $H_2SO_4$ were added and the solution was irradiated for 50 minutes (high pressure Hg lamp with a pyrex filter). The solvent was evaporated and the so obtained 10-hydroxy camptothecin was used for the following step (nitration) without any other purification.

The 10-hydroxy-20(S)-camptothecin was dissolved in 40 ml of $HNO_3$ (30%); after 1 hr 4 ml of $HNO_3$ (65%) were added. The reaction mixture was left at room temperature for 18 hours and then was extracted with $CH_2Cl_2$. The organic phase was washed with water till neutral, dried with $Na_2SO_4$ and evaporated to give 0.250 g of the title product.

$H^1NMR$ (DMSO-$d_6$), δ ppm: 0.86 (3H, t, J=7.3 Hz) ; 1.84 (2H, m); 5.23 (2H, s); 5.40 (2H, s); 6.51 (1H, s); 7.26 (1H, s); 7.6–8.2 (2H, m); 8.42 (1H, s).

Method B

A suspension of 20(S)-camptothecin (1 g) and prereduced $PtO_2$ (0.2 g) in a 1:1 mixture of acetic acid:dioxane (200 ml) was hydrogenated at room temperature and pressure until the mixture had adsorbed 2 equivalents of $H_2$. The suspension was filtered and the obtained solution was evaporated in vacuo to yield 0.6 g of a tetrahydroderivatives mixture.

Lead tetraacetate (2.1 g) was added to the crude tetrahydroderivative mixture (0.5 g) in trifluoroacetic acid (15 ml). The mixture was stirred at room temperature for 15 minutes, and then evaporated in vacuo. The crude 10-hydroxy-20(S)-camptothecin obtained was utilized for the subsequent step without further purification.

The 10-hydroxy-20(S)-camptothecin was dissolved in 40 ml of $HNO_3$ (30%); after 1 hr 4 ml of $HNO_3$ (65%) were added. The reaction was washed with water till neutral, dried with $Na_2SO_4$ and evaporated to give 0.250 g of the title product, which was identical to the compound obtained with method A.

EXAMPLE 2

9-nitro-10-(p-fluorobenzenesulfonvloxy)-20(S)-camptothecin

To a solution of 0.3 g of 9-nitro-10-hydroxy-20(S)-camptothecin in 20 ml of $CH_2Cl_2$, 0.17 g of p-fluorobenzsulfonylchloride and 0.12 ml of $Et_3N$ were added. After 1 hr the reaction mixture was treated with 10% HCl, then the organic phase was washed with water till neutral and dried with $Na_2SO_4$. The solvent was evaporated and the product purified by column chromatography to give 0.24 g of the title product.

$H^1NMR$ (DMSO-$d_6$), δ ppm: 0.86 (3H, t, J=7.3 Hz); 1.85 (2H, m); 5.26 (2H, s); 5.42 (2H, Abq); 7.37 (1H, s); 7.5–8.1 (5H, m); 8.53 (1H, d, J=9.9 Hz); 8.60 (1H, s).

EXAMPLE 3

9-nitro-10-trifluoromethansulphonyloxy-20(S)-camptothecin

A solution of 0.2 g of 9-nitro-10-hydroxy-20(S)-camptothecin and 0.08 ml of $Et_3N$ in 10 ml of $CH_2Cl_2$, in an argon atmosphere, was cooled to 0° C. 0.1 ml of trifluoromethansulfonic anhydride, dissolved in 1 ml of $CH_2Cl_2$ were dropped over 5 minutes into the solution. After 0.5 hr the reaction mixture was worked up as in Example 2. 0.18 g of 9-nitro-10-(trifluoromethansulfonyloxy)-20(S)-camptothecin were obtained after column chromatography.

$H^1NMR$ (DMSO-$d_6$), δ ppm: 0.86 (3H, t, J=7.3 Hz); 1.86 (2H, m); 5.31 (2H, s); 5.44 (2H, ABq); 6.58 (1H, s); 7.41 (1H, s); 8.2–8.7 (2H, m); 8.82 (1H, s).

EXAMPLE 4

9-nitro-10-(methansulphonyloxy)-20(S)-camptothecin 0.07 ml of methansulfonylchloride dissolved in 1 ml of $CH_2Cl_2$ were dropped over 5 minutes into a solution of 0.3 g of 9-nitro-10-hydroxy-20(S)-camptothecin in 15 ml of $CH_2Cl_2$ containing 0.122 ml of $Et_3N$, in an argon atmosphere, cooled to 0–5° C. After 0.5 hr the reaction mixture was worked up as in Example 2. 0.3 g of 9-nitro-10-(methansulfonyloxy)-20(S)-camptothecin were obtained after column chromatography.

$H^1NMR$ (DMSO-$d_6$), δ ppm: 0.86 (3H, t, J=7.7 Hz); 1.85 (2H, m); 3.70 (3H, s); 5.29 (2H, s); 5.43 (2H, s); 7.39 (1H, s); 8.1–8.6 (2H, m); 8.69 (1H, s).

EXAMPLE 5

9-amino-20(S)-camptothecin

To a solution of 0.1 g of 9-nitro-10-(p-fluorobenzensulfonyloxy)-20(S)-camptothecin in 2 ml of DMF, 0.1 ml of triethylamine, 0.028 ml of formic acid, 0.005 g of 1,1'-bis(diphenylphosphino)ferrocene and 0.002 g of $Pd(OAc)_2$ were added. The mixture was then heated to 80° C. for four hours. The solvent was evaporated in vacuo, and the crude reaction mixture was purified by column chromatography. The title product was obtained as a yellow solid (0.03 g).

$H^1NMR$ (DMSO-$d_6$), δ ppm: 0.87 (3H, t, J=7.3 Hz); 1.85 (2H, m); 5.26 (2H, s); 5.41 (2H, s); 6.11 (2H, s); 6.50 (1H, s); 6.79 (1H, m); 7.28 (1H, s); 7.3–7.5 (2H, m); 8.83 (1H, s).

EXAMPLE 6

9-amino-20(S)-camptothecin

To a solution/suspension of 0.1 g of 9-nitro-10-methansulphonyloxy-20(S)-camptothecin in 3 ml of dioxane, 0.04 ml of triethylamine, 0.011 ml of formic acid, 0.007 g of 1,1'-bis(diphenylphosphino)ferrocene and 0.003 g of $Pd(OAc)_2$ were added. The mixture was then heated at 90° C. for one hour. After one hour further 0.35 ml of a 1.8M solution of triethylammonium formate was added. After one hour the solvent was evaporated in vacuo, and the crude reaction mixture was purified by column chromatography. The title product was obtained as a yellow solid (0.06 g).

H$^1$NMR (DMSO-d$_6$), δ ppm: 0.87 (3H, t, J=7.3 Hz); 1.85 (2H, m); 5.26 (2H, s); 5.41 (2H, s); 6.11 (2H, s); 6.50 (1H, s); 6.79 (1H, m); 7.28 (1H, s); 7.3–7.5 (2H, m); 8.83 (1H, s).

EXAMPLE 7

9-amino-20(S)-camptothecin

To a solution of 0.1 g 9-nitro-10-trifluoromethansulphonyloxy-20(S)-camptothecin in 4 ml of dioxane, 0.25 ml of polymethylhydroxysiloxane, 0.004 g of 1,1'-bis(diphenylphosphino)ferrocene and 0.002 g of Pd(OAc)$_2$ were added. The mixture was then heated at 40° C. for three hours. The solvent was evaporated in vacuo, and the crude reaction mixture was purified by column chromatography. The title product was obtained as a yellow solid (0.036 g).

H$^1$NMR (DMSO-d$_6$), δ ppm: 0.87 (3H, t, J=7.3 Hz); 1.85 (2H, m); 5.26 (2H, s); 5.41 (2H, s); 6.11 (2H, s); 6.50 (1H, s); 6.79 (1H, m); 7.28 (1H, s); 7.3–7.5 (2H, m); 8.83 (1H, s).

EXAMPLE 8

9-nitro-12-hydroxv-20(S)-camptothecin

To a stirred solution/suspension of 12-nitro-20(S)-camptothecin (20 g) in conc. HCl (200 mL), anhydrous SnCl$_2$ (41.9 g) was added at 0–5° C., and the resulting mixture was stirred continuously at room temperature overnight. The solid is filtered and washed with small amounts of conc. HCl. The yellow solid was then suspended in water and the pH adjusted to about 2 with solid sodium bicarbonate added in portions. The solid was collected by filtration, washed with water till neutral, then with ethanol and diethyl ether. After drying 10.5 g of 12-amino-20(S)-camptothecin were obtained.

Sodium nitrite (2 g), in 30 ml water, was added to a solution of 12-amino-20(S)-camptothecin (1 g) in 35% H$_2$SO$_4$ (100 ml) at 0–5° C. with stirring. After 10 minutes, urea (1 g) was added and the reaction mixture was stirred for a further 10 minutes. The mixture was dropped into a flask containing an aqueous solution of CuNO$_3$ (20 g), and then Cu$_2$O (3 g) was added to the solution. The reaction mixture was stirred at room temperature for 30 minutes. The reaction mixture was then extracted with methylene chloride. The solvent was removed in vacuo and the residue was purified by column chromatography, to yield 0.65 g of 12-hydroxy camptothecin.

The product obtained from the above described preparation was nitrated as described in Example 1, method A and B. There were obtained 0.5 g of the title product.

EXAMPLE 9

9-nitro-12-(p-fluorobenzensulfonyloxy)-20(S)-camptothecin

The reaction was performed as described above in Example 2, except that 9-nitro-12-hydroxy-20(S)-camptothecin was used as starting material, to yield the title product.

EXAMPLE 10

9-nitro-12-trifluoromethansulphonyloxy-20(S)-camptothecin

The reaction was performed as described above in Example 3, except that 9-nitro-12-hydroxy-20(S)-camptothecin was used as starting material, to yield the title product.

EXAMPLE 11

9-nitro-12-(methansulphonvloxy)-20(S)-camptothecin

The reaction was performed as described above in Example 4, except that 9-nitro-12-hydroxy-20(S)-camptothecin was used as starting material, to yield the title product.

EXAMPLE 12

9-amino-20(S)-camptothecin

The reaction was performed as described above in Example 5, except that c-nitro-12-(p-fluorobenzensulfonyloxy)-20(S)-camptothecin was used as starting material, to yield the title product, which was identical to an authentic sample.

EXAMPLE 13

9-amino-20(S)-camptothecin

The reaction was performed as described above in Example 6, except that 9-nitro-12-methansulfonyloxy-20(S)-camptothecin was used as starting material, to yield the title product, which was identical to an authentic sample.

EXAMPLE 14

9-amino-20(S)-camptothecin

The reaction was performed as described above in Example 7, except that 9-nitro-12-trifluoromethansulfonyloxy-20(S)-camptothecin was used as starting material, to yield the title product, which was identical to an authentic sample.

EXAMPLE 15

9-amino-10-(p-fluorobenzensulphnyloxy)-20(S)-camptothecin 0.25 g of 9-nitro-10-(p-fluorobenzensulphonyloxy)-20(S)-camptothecin dissolved in 10 ml of dioxane were hydrogenated at room temperature and atmospheric pressure for 4 hours in the presence of 0.02 g of 10% Pd/C. The catalyst was filtered off and the solvent was removed in vacuo. The crude product was purified by chromatography to yield 0.2 g of the title product.

H$^1$NMR (DMSO-d$_6$), δ ppm: 0.86 (3H, t, J=7.3 Hz) ; 1.84 (2H, m); 5.23 (2H, s); 5.40 (2H, s); 6.00 (2H, s); 6.52 (1H, s); 7.28 (1H, s); 7.3–7.8 (6H, m); 8.83 (1H, s).

EXAMPLE 16

9-nitro-20(S)-camptothecin

To a solution of 0.1 g of 9-nitro-10-(p-fluorobenzensulfonyloxy)-20(S)-camptothecin in 2 ml of dioxane, 0.1 ml of triethylamine, 0.028 ml of formic acid, 0.0055 g of 1,1'-bis(diphenylphosphino)ferrocene and 0.002 g of Pd(OAc)$_2$ were added. The mixture was then heated to 80° C. for 30 minutes. The solvent was evaporated in vacuo, and the crude reaction mixture was purified by column chromatography. The title product was obtained as a yellow solid.

H$^1$NMR (DMSO-d$_6$), δ ppm: 0.87 (3H, t, J=7.3 Hz); 1.86 (2H, m); 5.33 (2H, s); 5.43 (2H, s); 6.56 (1H, s); 7.38 (1H, s); 8.0–8.6 (3H, m); 9.15 (1H, s).

EXAMPLE 17

9-amino-20(S)-camptothecin

A solution of 0.6 g of 9-nitro-20(S)-camptothecin in 7.5 ml of DMF was hydrogenated at room temperature and atmospheric pressure in the presence of 0.02 g of 10% Pd/C for four hours. The catalyst was filtered off, and washed with warm DMF repeatedly. The solution was evaporated in vacuo and the crude reaction mixture was purified by column chromatography, to yield the title product.

EXAMPLE 18

9-nitro-10-(p-toluensulfonyloxy)-20(S)-camptothecin

Operating as described in Example 2, but using p-toluensulfonyl chloride (0.16 g), the title compound (0.36 g) was obtained.

H$^1$NMR (DMSO-d$_6$), δ ppm: 0.86 (3H, t, J=7.3 Hz); 1.86 (2H, m); 2.44 (3H, s); 5.26 (2H, s); 5.42 (2H, ABq); 6.56 (1H, s); 7.37 (1H, s); 7.5–8.0 (5H, m); 8.51 (1H, d, J=9.8 Hz); 8.59 (1H, s).

EXAMPLE 19

9-amino-20(S)-camptothecin

The reaction was performed as described in Example 5, except that 9-nitro-10-(p-toluensulfonyloxy)-20(S)-camptothecin was used as starting material to yield the title product, which was identical to the sample obtained in Example 5.

EXAMPLE 20

9-nitro-20(S)-camptothecin

The reaction was performed as described in Example 16, except that 9-nitro-10-(p-toluensulfonyloxy)-20(S)-camptothecin was used as starting material to yield the title product, which was identical to the sample obtained in Example 16.

EXAMPLE 21

9-amino-10-(p-toluensulfonyloxy)-20(S)-camptothecin

A solution of 0.1 g of 9-nitro-10-(p-toluensulfonylxy)-20 (S)-camptothecin in 5 ml of DMF was hydrogenated at room temperature and atmospheric pressure in the presence of 0.025 g of prereduced PtO$_2$ for 24 hours. The catalyst was removed by filtration, and the solution was concentrated in vacuo. The crude reaction mixture was purified by column chromatography, to yield the 0.05 g of the title product.

H$^1$NMR (DMSO-d$_6$), δ ppm: 0.87 (3H, t, J=7.3 Hz); 1.84 (2H, m); 2.37 (3H, s); 5.23 (2H, s); 5.40 (2H, s); 5.98 (2H, s); 6.50 (1H, s); 7.2–7.5 (5H, m); 7.83 (2H, m); 8.85 (1H, s).

We claim:

1. A compound of formula (V) or (VII)

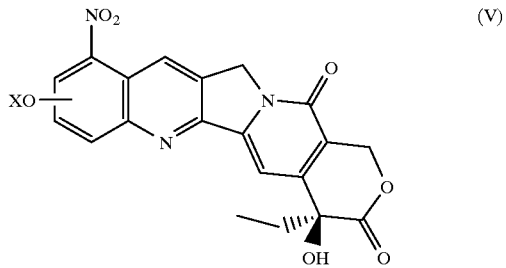

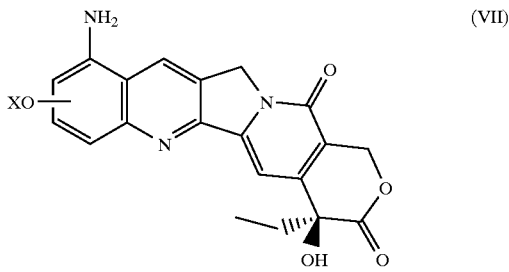

wherein X is R—SO$_2$— in which
R is:
(i) a phenyl or naphthyl ring which is unsubstituted or substituted by one substituent chosen from C$_1$–C$_5$ linear or branched alkyl, C$_1$–C$_5$ linear or branched alkoxy, halogen, hydroxy, amino and nitro; or
(ii) a linear or branched C$_1$–C$_9$ alkyl group which is unsubstituted or substituted by one or more halogen atoms, or a pharmaceutically acceptable salt thereof.

2. The compound of formula (V) according to claim 1 which is 9-nitro-10-(p-toluensulfonyloxy)-20((S)-camptothecin and the pharmaceutically acceptable salts thereof.

3. The compound of formula (VII) according to claim 1 which is 9-amino-10-(p-toluensulfonyloxy)-20((S)-camptothecin and the pharmaceutically acceptable salts thereof.

4. A pharmaceutical composition which comprises as an active compound, a compound of formula (V) or (VII), as defined in claim 1, or a pharmaceutically acceptable salt thereof, and a pharmaceutically acceptable carrier and/or diluent.

5. A method of treating tumors comprising administering to a patient in need thereof a therapeutically effective amount of a compound of formula (V) or (VII) according to claim 1, or a pharmaceutically acceptable salt thereof, wherein said tumor is susceptible to camptothecin.

6. A method of treating tumors, said method comprising administering a pharmaceutical composition according to claim 4 to a patient in need thereof, wherein said tumor is susceptible to camptothecin.

* * * * *

UNITED STATES PATENT AND TRADEMARK OFFICE
CERTIFICATE OF CORRECTION

PATENT NO. : 5,916,897
DATED : June 29, 1999
INVENTOR(S) : Walter CABRI, et al.

It is certified that error appears in the above-identified patent and that said Letters Patent is hereby corrected as shown below:

On the title page, item [62] the Related U.S. Application Data should be:

--[62] Division of application No. 08/313,906, Sep. 28, 1994, Pat. No. 5,614,628--

Signed and Sealed this

Sixteenth Day of May, 2000

Attest:

Q. TODD DICKINSON

*Attesting Officer*          *Director of Patents and Trademarks*